United States Patent [19]
Noda

[11] Patent Number: 5,983,670
[45] Date of Patent: Nov. 16, 1999

[54] JEWELS FOR LIVE OR ARTIFICIAL TOOTH OR TEETH

[76] Inventor: Satoshi Noda, Verde Machida 1410, 1-7-2, Haramachida, Machida-shi, Tokyo, Japan

[21] Appl. No.: 08/917,956

[22] Filed: Aug. 27, 1997

[30] Foreign Application Priority Data

Jun. 17, 1997 [JP] Japan ................................. 9-176494

[51] Int. Cl.⁶ .................................................. A44C 17/02
[52] U.S. Cl. ...................................... 63/26; 63/27; 63/33
[58] Field of Search .................................. 63/26, 27, 33

[56] References Cited

U.S. PATENT DOCUMENTS

| 1,389,031 | 8/1921 | Cumming | 63/26 |
| 1,754,964 | 4/1930 | Pancoast | 63/26 X |
| 2,596,965 | 5/1952 | Troy | 63/26 X |
| 5,431,028 | 7/1995 | Lampert et al. | 63/26 X |

FOREIGN PATENT DOCUMENTS

| 2579428 | 10/1986 | France | 63/26 |
| 1170184 | 5/1964 | Germany | 63/27 |
| 666996 | 9/1988 | Switzerland | 63/26 |

*Primary Examiner*—Brian K. Green
*Assistant Examiner*—Andrea Chop
*Attorney, Agent, or Firm*—Jordan and Hamburg LLP

[57] ABSTRACT

A tooth or teeth jewels comprising highly clear gems such as diamond, zirconia, quartz, white sapphire or the like fixed as partially buried in a concavity formed in a live or artificial tooth or teeth, the tooth or teeth jewels being secured to the tooth or teeth by means of a gem retainer made of a high-reflectance metal or resin which provides a golden, silver or platinum color and/or brilliance, or by means of a combination of the gem retainer and a colored reflective film.

14 Claims, 7 Drawing Sheets

JEWELS FOR LIVE OR ARTIFICIAL TOOTH OR TEETH

BACKGROUND OF THE INVENTION

1. Field of the Invention

The present invention relates to a tooth or tooth jewels comprising a highly clear gem Such as diamond, zirconia, quartz, white sapphire, etc. fixed as partially buried in a concavity formed in a live or artificial tooth or teeth.

2. Description of the Prior Art

These days, we can enjoy a wide variety of ornaments or fashions, one of which is to enhance the originality of an ornament put on one's clothing or directly on one's body. For this application, various kinds of jewels, ornaments and accessories have been developed.

Necklace, bracelet, earring, ornament with ear wire, etc. are very popular. In addition, coloring the hairs and direct decoration of the fingernails or toenails, for example, have also been included in the recent fashionable modes of ornamenting. Furthermore, some people have a jewel attached directly to a live or artificial tooth to ornament their teeth.

In case of a ring jewel, for example, namely, when a gem is laterally supported by prongs in such a manner that the contact area of the prongs with the gem is as small as possible, the light incident upon the gem will not be so much absorbed at the inner walls of the prongs. Thus the brilliance of the gem can be assured by the reflection and scattering of the light through the gem.

However, in case a gem is used as fixed in a concavity formed in a live or artificial tooth (false tooth), the gem has a nearly half of the whole surface area (entire pavilion or rear surface) thereof buried in the concavity. In other words, the light incident upon the gem is easily absorbed by the tooth. More particularly, the majority of external light incident upon the gem, reaching the rear surface of the gem and passing through the gem is absorbed by the tooth behind the gem. This will result in a remarkably reduced reflectance of the light, so that the gem will not present its full brilliance and color which could be assured when the gem is used in a ring jewel, for example.

SUMMARY OF THE PRESENT INVENTION

Accordingly, the present invention has an object to overcome the drawbacks of the prior art by providing a tooth jewel destined for use on a live or artificial tooth for ornamenting the teeth with 110 substantial missing of its color and brilliance.

The above object is accomplished by providing a tooth jewel comprising a highly clear gem such as diamond, zirconia, quartz, white sapphire, etc. fixed as partially buried in a concavity formed in a live or artificial tooth or teeth, and a gem setting of retainer secured to the pavilion or rear surface of the gem and made of a high-reflectance metal or synthetic resin having a golden, silver or platinum color and/or brilliance, the gem retainer being constricted at an intermediate position between the outer and the inner ends thereof and thicker as it goes from the constricted portion toward the inner end, and the gem being to be secured to the tooth by means of the gem retainer.

According to another aspect of the present invention, a tooth jewel is provided which comprises a highly clear gem such as diamond, zirconia, quartz, white sapphire, etc. fixed as partially buried in a concavity formed in a live or artificial tooth or teeth, a gem retainer made of a metal or synthetic resin, and a high-reflectance colored film provided on the inner surface of the gem retainer that is in contact with the gem or on the rear of the gem that is in contact with the gem retainer, respectively, to selectively reflect a light ray or rays of a predetermined wavelength or wavelengths, respectively, for thereby providing a golden, silver or platinum color and/or brilliance.

According to a still another aspect of the present invention, a tooth jewel is provided which comprises a highly clear gem such as diamond, zirconia, quartz, white sapphire, etc. fixed as partially buried in a concavity formed in a live or artificial tooth or teeth, a light-transparent retainer made of a metal or synthetic resin, and a high-reflectance colored film provided on the outer surface of the gem retainer to selectively reflect toward the gem light of a predetermined wavelength, respectively, having passed and traveled through the gem and gem retainer, for thereby providing a golden, silver or platinum color and/or brilliance.

In the tooth jewel according to the present invention, external light incident upon the gem is reflected at the high-reflectance metal or synthetic resin or colored film provided on the pavilion of the gem and which provides the golden, silver or platinum color and/or brilliance, so the light having passed through the gem shows a predetermined color and also the tooth appears bright.

These objects and other objects, features, aspects and advantages of the present invention will become more apparent from the following detailed description of the present invention when taken in conjunction with the accompanying drawings.

DETAILED DESCRIPTION OF THE PREFERRED EMBODIMENTS

Figure 1:
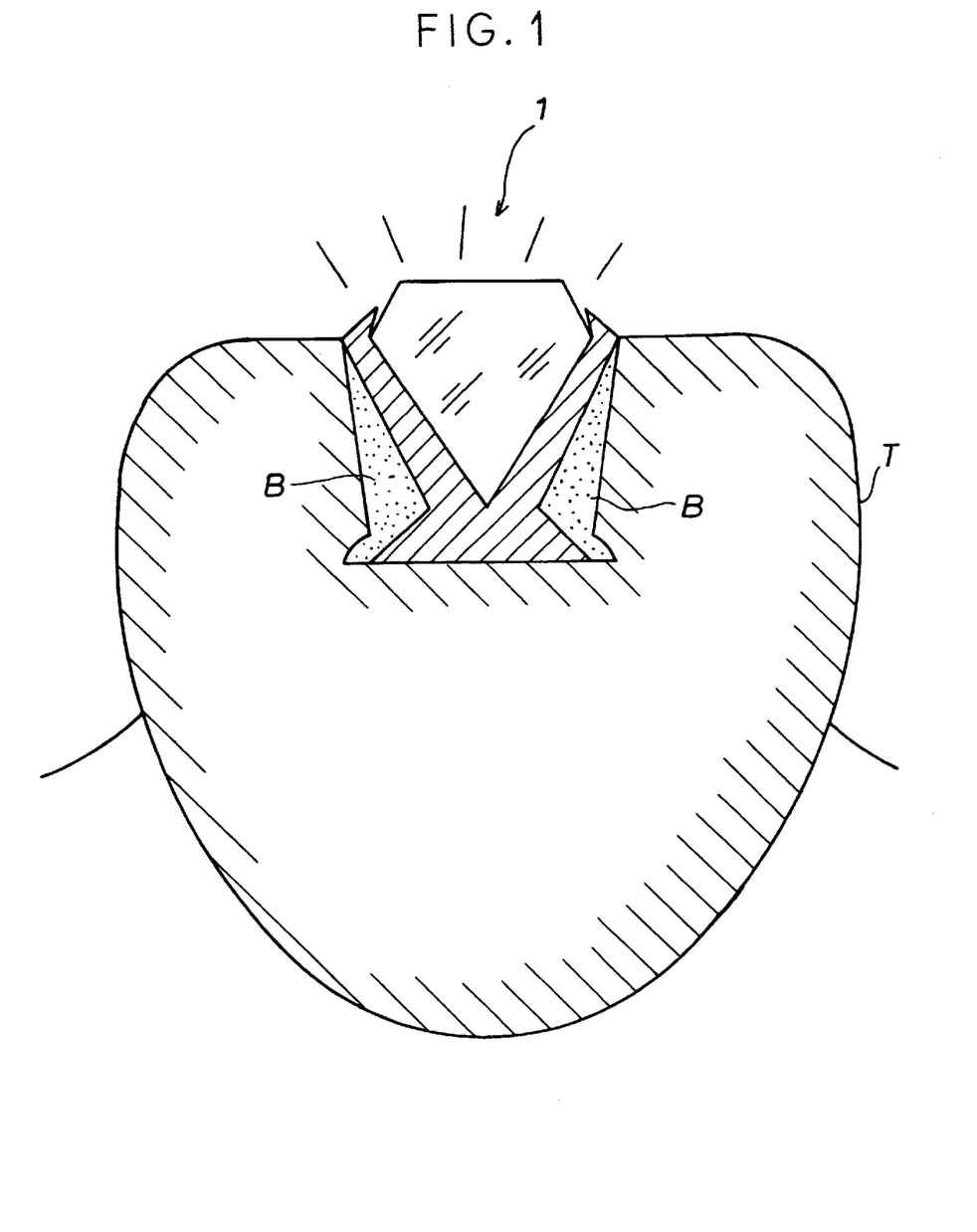
FIG. 1 is an explanatory drawing showing a tooth jewel according to the present invention, used on a live or artificial tooth.

FIG. 1 shows a tooth jewel 1 according to the present invention is secured to a tooth T (the present invention is applicable to an artificial or false tooth or teeth or a live tooth or teeth).

Figure 2:
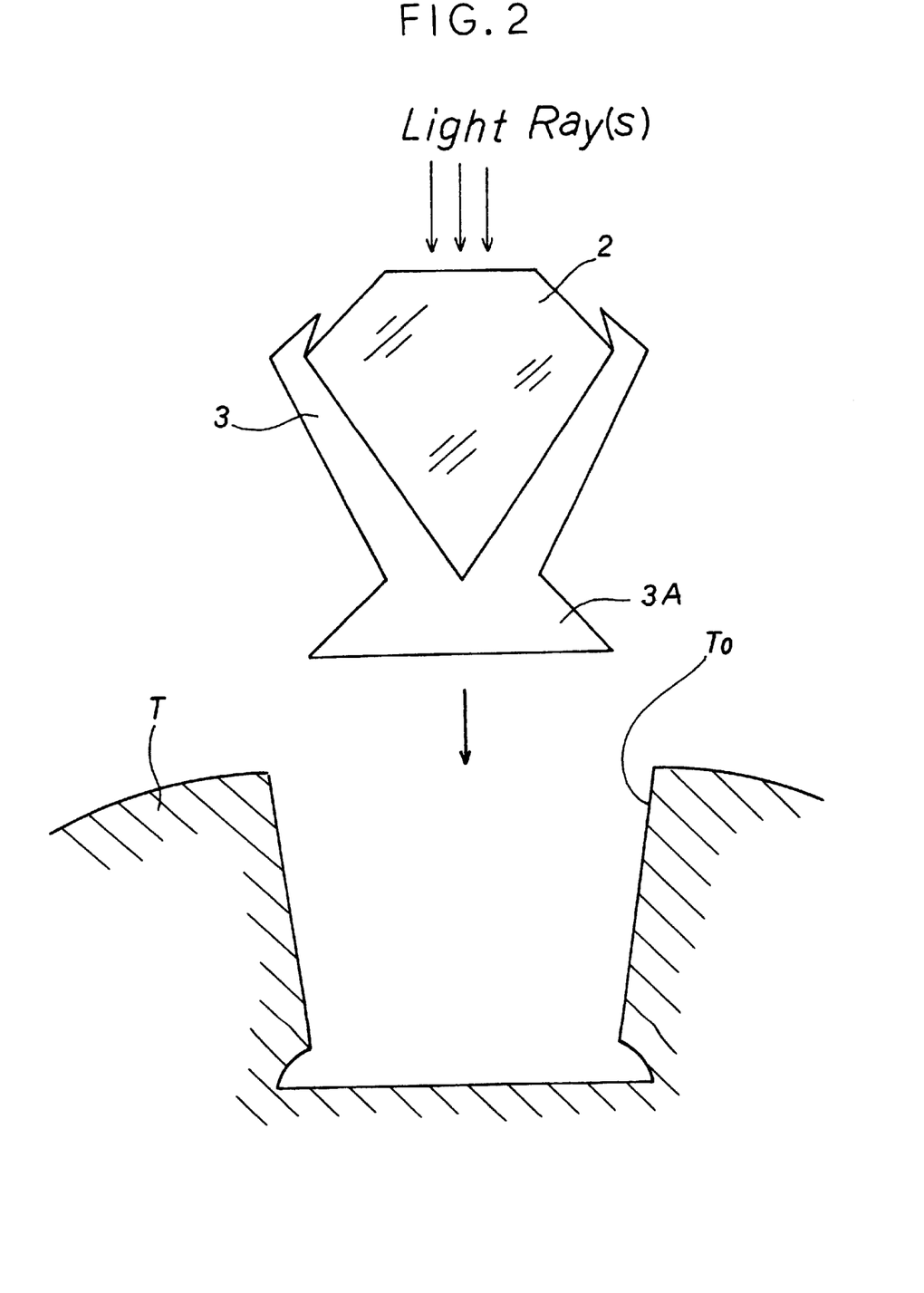
FIG. 2 is an explanatory drawing showing how to attach the jewel in FIG. 1.

The tooth jewel 1 is partially buried in a concavity $T_0$ formed on the surface of a tooth T as shown in FIG. 2 and secured to the tooth T with an appropriate adhesive B (as in FIG. 1).

Figure 3:
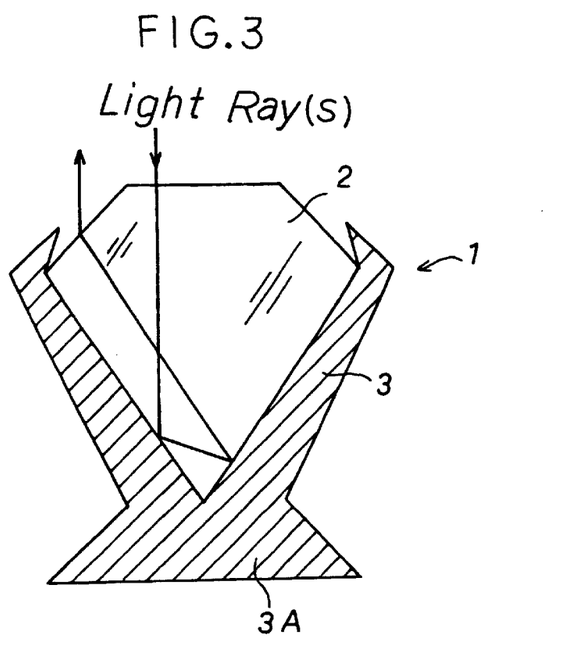
FIG. 3 is a schematic sectional view of a first embodiment of the present invention.

FIG. 3 shows the first embodiment of the present invention. In this embodiment, the tooth jewel 1 comprises a highly clear gem 2 such as diamond, zirconia (colored), quartz, white sapphire, etc. which is of course excellent in color, brightness, reflectance, light scattering property and other properties the excellent gems own, and a gem retainer 3 embracing to retain the gem 2 at the pavilion or rear surface of the latter.

The gem retainer 3 is made of an appropriate metal or synthetic resin having a golden, silver or platinum color or brilliance, and provides a means of selectively reflecting only light of a predetermined wavelength (color). In this embodiment, the gem retainer 3 is made of a high-reflectance metal such as gold (Au), platinum (Pt), silver (Ag), aluminum (Al) or the like, or an appropriate synthetic resin given a bright color such as gold, silver or platinum, red, blue, yellow, green, purple or the like (to selectively absorb light rays of any wavelengths other than the predetermined one or ones). Note that the gem retainer 3 should preferably be secured to the tooth with an appropriate adhesive (not shown) highly transparent to light and absorbing possible light, but the gem retainer 3 may be fixed directly to the tooth, not using any such adhesive.

Also, the gem retainer 3 is tapered toward the inner end thereof and constricted at an intermediate position between the outer and inner ends thereof, and then thicker (as indicated at 3A) as it goes from the constricted portion toward the inner end to prevent the gem retainer 3 from easily being disengaged from the tooth after secured in the concavity $T_0$ in the tooth. After the gem 2 is fixed at the rear surface thereof in the gem retainer 3, the latter 3 is secured in the concavity in the tooth with the appropriate adhesive B. Different from the adhesive used to fix the gem retainer 3 to a tooth as mentioned above, the adhesive B may not be so high light-transparent and absorb possible light.

Figure 4:
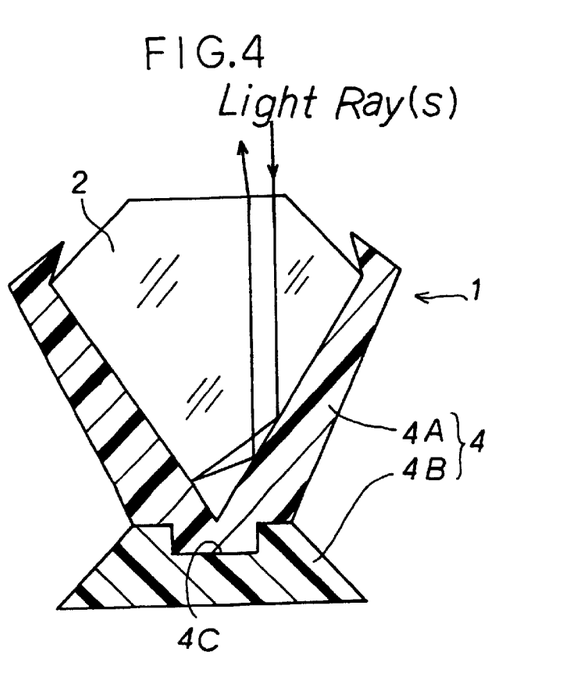
FIG. 4 is a schematic sectional view of a variant of the first embodiment in FIG. 3.

It should be noted that, as in the variant of the present invention shown in FIG. 4, the gem retainer 3 may be composed of two portions: a first portion 4A made of a metal or synthetic resin having a golden, silver or platinum color and brilliance and which is to be in contact at the outer surface thereof with the wall of the concavity $T_0$ formed in the tooth, the first portion 4A being tapered toward the inner end thereof and having a projection formed at the bottom thereof, and a second portion 4B having formed therein a concavity 4C in which the projection of the first portion 4A is to be fitted and secured. The first and second portions 4A and 4B are thus joined to each other to form the gem retainer 3 as a whole.

Figure 5:
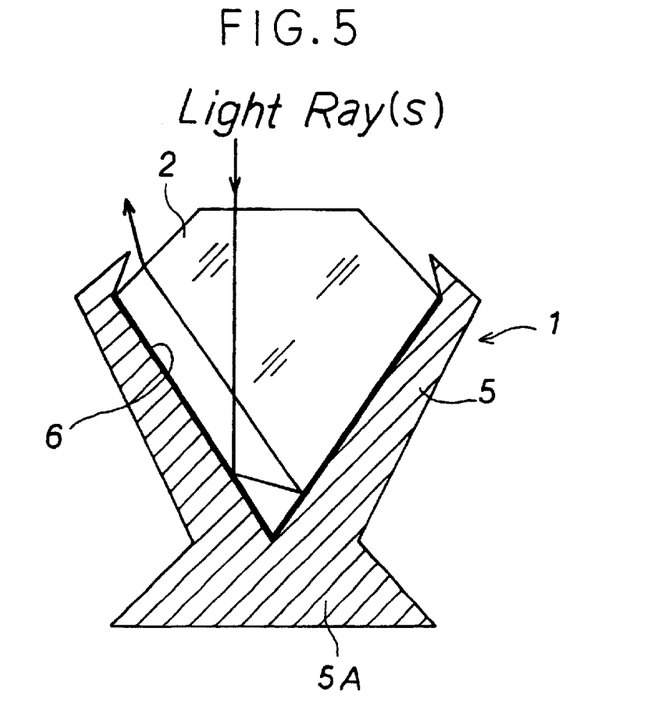
FIG. 5 is a schematic sectional view of a second embodiment of the present invention.

The second embodiment of the present invention will be described herebelow with reference to FIG. 5.

According to this embodiment, the tooth jewel 1 comprises the gem 2, a gem retainer 5 embracing to retain the gem 2 on the inner wall thereof, and a colored reflective film 6 provided on the inner wall of the gem retainer 5 (or outer surface of the gem 2 that is to be in contact with the inner wall of the gem retainer 5) to selectively reflect light of a predetermined wavelength, respectively, to provide a golden, silver or platinum color and brilliance. The gem retainer 5 is tapered toward an intermediate position as in the first embodiment and variant having been described in the foregoing. In FIG. 5, the reference numeral 5A indicates a portion of the gem retainer 5 that is thicker as it goes toward the inner end of the gem retainer 5. That is to say, the gem retainer 5 is constricted at the intermediate position as in the first embodiment and variant.

In this embodiment, the gem retainer 5 may be made of an appropriate metal or synthetic resin.

Also, the colored reflective film 6 may be made of an appropriate material. To selectively reflect effectively only ones of predetermined wavelengths of the light rays having passed through the gem 2, the reflective film 6 may be made of a gold, silver or aluminum sheet (which is satisfactory only for reflecting the light rays of predetermined wavelengths; for more than that, however, it is necessary to color the film 6 for thereby selectively absorbing light rays). However, the film 6 should more preferably be made of a dielectric multi-layer sheet which can selectively reflect only the light rays of predetermined wavelengths highly effectively. Note that the dielectric multi-layer sheet referred to herein may be a one made of an odd number of layers, 13 or 15 layers, including layers of a transparent material having a high refraction index such as $ZnS$, for example, and other layers made of a material having a low refractive index such as $MgF_2$, for example, the former and latter layers being alternately laminated one on another by evaporation. The lamination is made by evaporation or any other suitable means, not using any adhesive. However, when an adhesive is used for this purpose, it should preferably be a one highly light-transparent and absorbs possible light.

Figure 6:
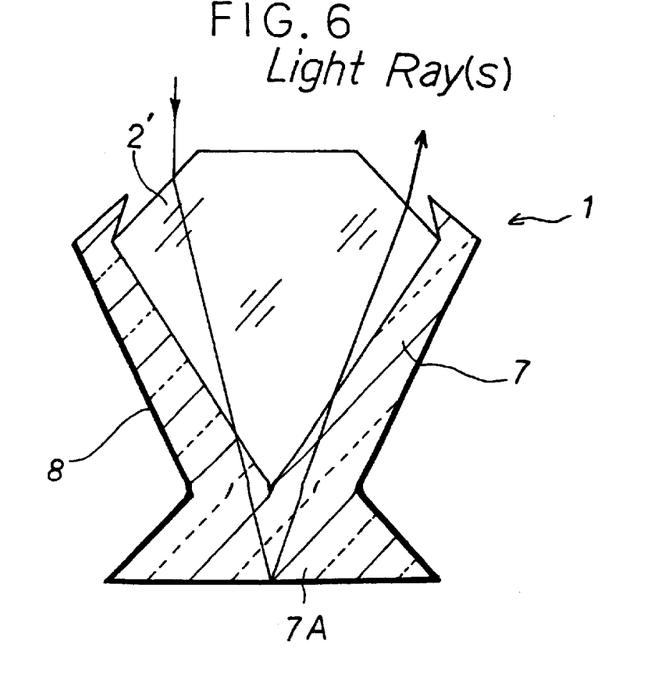
FIG. 6 is a schematic sectional view of a third embodiment of the present invention.

FIG. 6 shows the third embodiment of the present invention. The tooth jewel 1 in this embodiment comprises a gem 2' of a same kind as those in the aforementioned first and second embodiments, a light-transparent gem retainer 7 which embraces to retain the gem 2' at the rear surface of the latter, and a colored reflective film 8 provided on the outer surface of the gem retainer 7 to selectively reflect light rays of predetermined wavelengths, for thereby providing a golden, silver or platinum color and brilliance. In FIG. 6, the reference numeral 7A indicates a portion of the gem retainer 7 which is thicker as it goes toward the inner end of the gem retainer 7. That is to say, the gem retainer 7 is constricted at the position near the inner end thereof as in the aforementioned first embodiment, variant and second embodiment.

The transparent gem retainer 7 is made of an appropriate synthetic resin having a high light-transparency and some rigidity. It can be fixed directly to the tooth T, but it may be secured to the tooth with a suitable adhesive (which also should preferably highly transparent to light).

The colored reflective film 8 is made of a material similar to that used in the second embodiment. Namely, it may be an appropriate silver or aluminum sheet, for example, which however should be able to selectively reflect light rays. It also may be made of a dielectric multi-layer sheet or the like.

According to this embodiment, the colored reflective film 8 is provided to impart a desired color and brilliance to the gem 2'. However, the light-transparent gem retainer 7 may be colored and a simple reflective film (for example, a gold, silver or aluminum thin film) may be provided in place of the colored reflective film 8.

Figure 7:
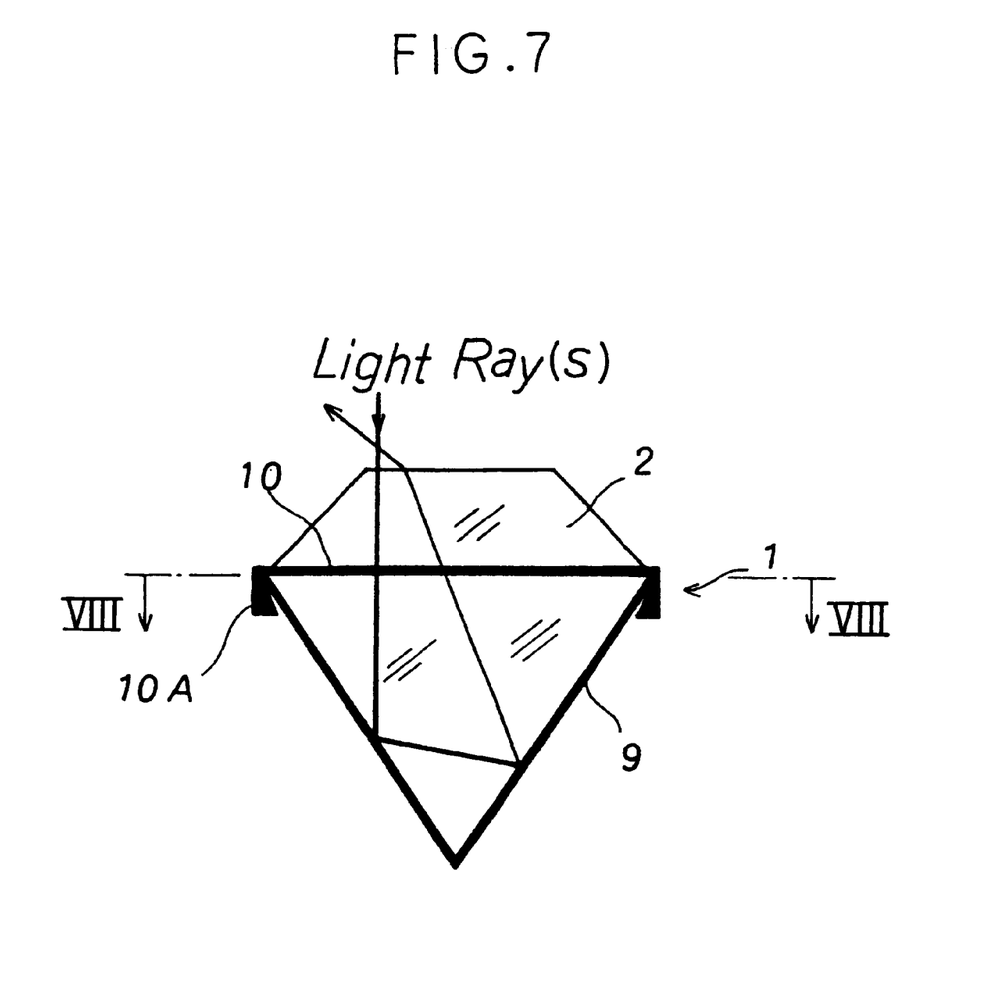
FIG. 7 is a schematic sectional view of a fourth embodiment of the present invention.
Figure 8:
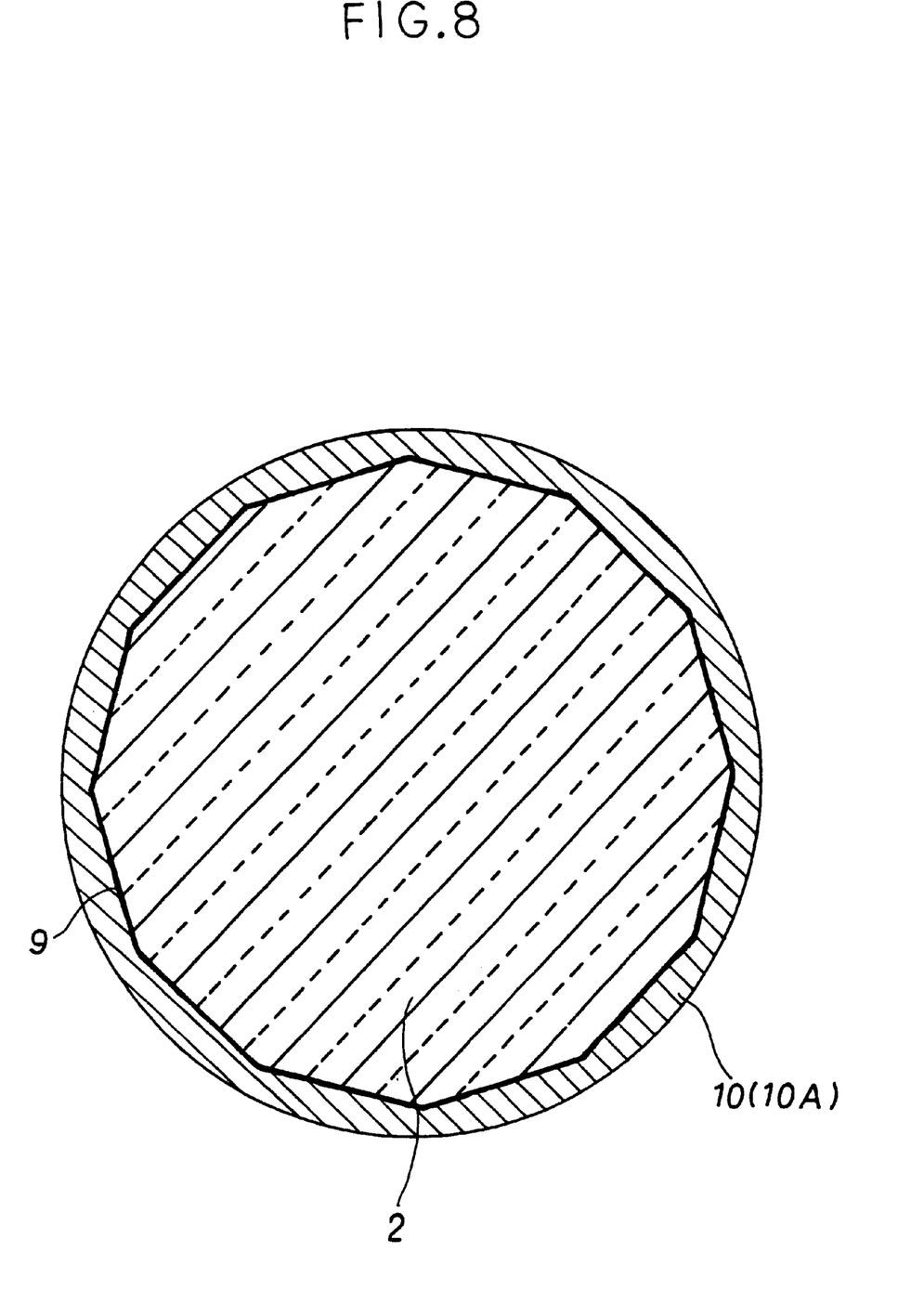
FIG. 8 is a sectional view taken along the line A—A in FIG. 7.

Next, the fourth embodiment of the present invention will be discussed with reference to FIGS. 7 and 8 herebelow.

The tooth jewel 1 according to this embodiment comprises a gem 2 similar to those used in the first and second embodiments having been described in the foregoing, a colored reflective film 9 provided on the pavilion or rear surface of the gem 2 to selectively reflect light rays of predetermined wavelengths to provide golden, silver or platinum color and brilliance, and a gem retainer 10 secured around the girdle of the gem 2.

The colored reflective film 9 used in this embodiment is similar to those used in the second and third embodiments. It is formed using no adhesive but by evaporation or other suitable means.

The gem retainer 10 is formed generally like a ring from a similar material to those for the gem retainer 3 in the first embodiment and the gem retainer 5 in the third embodiment. To prevent the retainer 10 from being easily disengaged from the tooth, it is tapered outwardly (as shown at 10A). The gem retainer 10 is to be fitted like a cap onto the gem 2 after the colored reflective film 9 provided on the gem 2.

Figure 9:
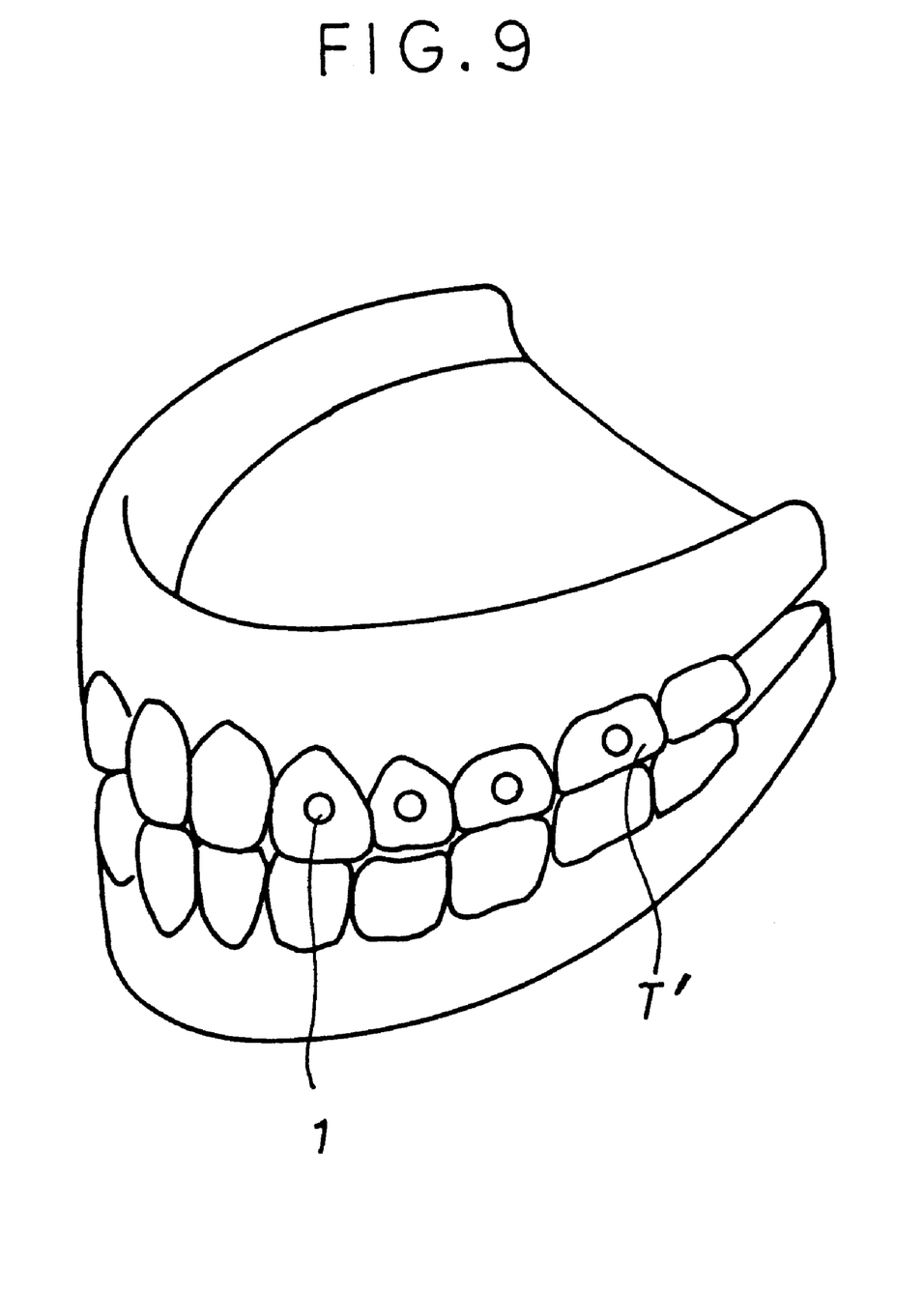
FIG. 9 is a schematic perspective view of an application of the present invention to a full set of false teeth.

The tooth jewel according to each of the aforementioned embodiments may be fixed to a live tooth as previously described. As shown in FIG. 9, however, the tooth jewel 1 may be used on all the upper ones or on some selected ones of a full set of false teeth. One tooth jewel or more is used on each tooth. The jewel 1 may also be used on some selected ones or all of the lower teeth, or it may be used only on the lower teeth.

As having been described in the foregoing, the gem is provided on the rear surface thereof with the colored reflective film which selectively reflects light rays of predetermined wavelengths to provide a golden, silver or platinum color and/or brilliance. When the tooth jewel is fixed in a live or artificial tooth or teeth, external light incident upon the gem in the tooth passes through the gem and is reflected at the reflective film behind the gem, and thus goes out of the tooth through the gem. Therefore, the tooth jewel according to the present invention can provide a further more enhanced color and brilliance than the conventional tooth jewels simply attached on the teeth. Thus, the tooth jewel according to the present invention will be a higher-grade ornament.

Also since the gem retainer itself is so constructed according to the present invention as to selectively reflect light rays of predetermined wavelengths, for example, only golden, silver or platinum color, the light reflected at the gem retainer and going out of the gem can have an enhanced color and/or brilliance. Therefore, the tooth jewel according to the present invention provides a considerably ornamental value.

What is claimed is:

1. A tooth ornament, comprising:

a highly light-transmissive gem; and a gem retainer fixed to a rear surface of the gem and securable in a concavity formed in one of a live and an artificial tooth;

the gem retainer including an outward end into which the gem is fixed and an opposite base end, and an intermediate position therebetween, the gem retainer presenting an outermost surface structure which includes an indentation, deepest at the intermediate position, defined by a gradual inward tapering of the retainer from the outward end to the intermediate position and a gradual outward widening of the retainer from the intermediate position to the base end, the gem retainer being made of at least one of a metal and a resin having a characteristic which selectively reflects a ray of light of predetermined wavelength while absorbing rays of light of other wavelengths.

2. A tooth ornament according to claim 1, wherein the gem retainer includes:

a coloring portion disposed as an inner wall of the gem retainer and made of a high-reflectance metal having one of a golden, silver and platinum color and brilliance; and a base portion having a concavity formed therein in which the coloring portion is fitted and secured.

3. A tooth ornament according to claim 1, wherein the artificial tooth is included in a set of false teeth.

4. A tooth ornament according to claim 1, wherein the gem retainer is made of a high-reflectance metal having one of a golden, silver and platinum color.

5. A tooth ornament according to claim 1, wherein the gem retainer is made of a resin having a bright color.

6. A tooth ornament according to claim 1 in combination with an artificial tooth, wherein:

the concavity formed in the artificial tooth has an inner wall which gradually tapers inwardly from an entry end of the concavity towards an intermediate point and which widens outwardly from the intermediate point to a bottom of the concavity.

7. A tooth ornament according to claim 1, wherein the gem retainer includes:

a coloring portion disposed as an inner wall of the gem retainer and made of a resin having a bright color; and a base portion having a concavity formed therein in which the coloring portion is fitted and secured.

8. A tooth ornament, comprising:

a gem retainer;

a gem at least partially received in said gem retainer and fixed thereto, said gem being exposed at an outward end of the gem retainer and a remainder of said gem extending inward of said gem retainer towards a base thereof; and said gem retainer being receivable in a concavity formed in a tooth for fixation therein, an outside dimension of said gem retainer being tapered over at least a portion of a distance extending from each of said outward end and said base towards an intermediate region lying between said outward end and said base thereby defining an indentation in an outermost surface structure of said retainer, said outside dimension being narrowest at said intermediate region and widening approaching each of said outward end and said base.

9. A tooth ornament according to claim 8, wherein at least a portion of said gem surrounded by said gem retainer is in contact with an interior of said gem retainer.

10. A tooth ornament according to claim 9, wherein said gem retainer is comprised of a material having a characteristic which selectively reflects a ray of light of predetermined wavelength while absorbing rays of light of other wavelengths.

11. A tooth ornament according to claim 8, wherein at least a portion of said gem retainer is comprised of a resin.

12. A tooth ornament according to claim 8, wherein at least a portion of said gem retainer is comprised of a metal.

13. A tooth ornament according to claim 8, in combination with a set of false teeth, and wherein said tooth is one of said false teeth.

14. A tooth ornament according to claim 8, wherein:

the gem retainer includes a first part and a second part, said first part comprising a portion of said gem retainer defining outer structure of said gem retainer extending between said outward end and said intermediate region, and said second part comprising another portion of said gem retainer defining outer structure of said gem retainer extending between said base and said intermediate region when said first and second parts are joined to one another.

* * * * *